United States Patent [19]

Jessel, Jr. et al.

[11] Plant 4,470

[45] Oct. 30, 1979

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 952,257

[22] Filed: Oct. 17, 1978

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Donald D. Jeffery

[57] ABSTRACT

An incurved capitulum type of chrysanthemum plant which is a sport of the non-commercial cultivar Arcade, disclosed in U.S. Plant Pat. No. 3,659, granted Nov. 26, 1974, Starcade being distinguished from the parent cultivar by its taller height, larger flower size and slower flowering response.

1 Drawing Figure

The present invention comprises a new and distinct cultivar of *Chrysanthemum morifolium,* Ramat., hereinafter referred to by the cultivar name of Starcade.

Starcade is a product of a planned sport induction program which had the objective of expanding the commercial value of the cultivar Arcade, disclosed in our U.S. Plant Pat. No. 3,659, granted Nov. 26, 1974.

Starcade was discovered and selected by William E. Duffett and Walter H. Jessel, Jr. on June 18, 1975 as one plant within a flowering block of the parental cultivar in a controlled environment in Barberton, Ohio. Plants within the flowering block were derived from stock plants which had been irradiated as rooted cuttings with an x-ray source of 2600 r units.

The first act of asexual reproduction of Starcade was accomplished when vegetative cuttings were taken from the initial selection in February, 1975 in a controlled environment in Barberton, Ohio. by a technician working under formulations established and supervised by Walter H. Jessel, Jr. and William E. Duffett. Continued asexual reproduction by vegetative cuttings for evaluative tests in flowering and stock programs in conjunction with horticultural examination of selected units initiated Jan. 30, 1976 has demonstrated that the combination of characteristics as herein disclosed for Starcade are firmly fixed and are retained through successive generations of asexual reproduction.

Starcade has not been observed under all possible environmental conditions. The phenotype may vary significantly with variations in environment such as temperature, light intensity and daylength. The following observations, measurements, and comparisons describe plants grown in Barbarton, Ohio and in Salinas, Calif. under greenhouse environmental conditions which approximate those generally used in commercial practice.

The following traits have been repeatedly observed and are determined to be basic characteristics of Starcade which in combination distinguish this chrysanthemum as a new and distinct cultivar:

(1) Standard capitulum type.

(2) Incurved capitulum form.

(3) White ray floret color.

(4) Diameter across face of capitulum ranging from 145 to 170 mm. at maturity.

(5) Uniform eight week photoperiodic flowering response to short days.

(6) Medium plant height (requires 1-3 long day weeks prior to short days to attain a flowered plant height of 77 to 82 cm. when grown as a single stem plant for April through November flowerings).

(7) Excellent shipping durability.

The accompanying color photographic drawing shows typical inflorescence and foliage characteristics of Starcade, with color depiction being as nearly true as possible with color illustrations of this type.

Of the many commercial cultivars known to the present inventors, the most similar existing cultivar in comparison to Starcade is Albatross (unpatented). Reference is made to attached Chart A which compares certain characteristics of Starcade with the same characteristics of Albatross. Comparisons to the parental cultivar, Arcade, are also included. General comparisons are as follows:

(1) In comparison to Albatross, Starcade has whiter ray floret color, larger diameter across face of capitulum, and taller plant height. The shipping durability, flowering response period, capitulum form, and capitulum type of Starcade are similar to those same characteristics of Albatross.

(2) In comparison to Arcade, Starcade has a larger diameter across the face of capitulum, taller plant height, and longer flowering response period. The ray floret color, shipping durability, capitulum type, and capitulum form of Starcade are similar to those same characteristics of Arcade.

In the following description, color references are made to A Limit Color Cascade, published by the Munsell Company, 1972 edition. The color values were determined between 9:30 and 10:00 A.M. on May 17, 1978 under 90 foot-candle light intensity at Salinas, Calif.

Botanical classification: *Chrysanthemum morifolium,* Ramat., cv. Starcade.

I. INFLORESCENSE

A. Capitulum:

*Form.*—Incurved.

*Type.*—Standard.

*Permanence.*—14 to 18 days.

*Diameter across face.*—145 to 170 mm.

B. Corolla of ray florets:

*Color (abaxial).*—White.

*Color (immature center).*—23-4 to 23-6.

*Color (adaxial).*—White.

C. Reproductive organs:

*Androecium.*—Present disc florets; scant to few; scant pollen.

*Gynoecium.*—Present both ray and disc florets.

II. PLANT

A. General appearance: Semi-upright branching pattern; medium plant height.

B. Foliage:

*Color (abaxial).*—Approximately 19-15.

*Color (adaxial).*—Approximately 20-13 to 20-14.

CHART A

Comparison of Starcade, Albatross, and Arcade

| Cultivar | Ray Floret Color | Diameter Across Face of Capitulum | Plant Height | Shipping Durability | Flowering Response Period | Capitulum Form and Type |
|---|---|---|---|---|---|---|
| Starcade | White | 145 to 170 mm. | Medium, 77 to 82 cm. | Excellent | 8 week | Incurved Standard |

CHART A – Continued

Comparison of Starcade, Albatross, and Arcade

| Cultivar | Ray Floret Color | Diameter Across Face of Capitulum | Plant Height | Shipping Durability | Flowering Response Period | Capitulum Form and Type |
|---|---|---|---|---|---|---|
| Albatross | Ivory white | 125 to 150 mm. | Short, 60 to 70 cm. | Excellent | 8 week | Incurved Standard |
| Arcade | White | 140 to 165 mm. | Short 65 to 75 cm. | Excellent | 7 week | Incurved Standard |

Comparisons Made of Plants Grown in a Greenhouse in Barberton, Ohio and in Salinas, California.

We claim:

1. A new and distinct cultivar of *Chrysanthemum morifolium;* Ramat., known by the cultivar name Starcade and particularly characterized as to uniqueness by the combined characteristics of standard capitulum type, incurved capitulum form, white ray floret color, diameter across face of capitulum ranging from 145 to 170 mm. at maturity, uniform eight week flowering response, medium plant height, and excellent shipping durability.

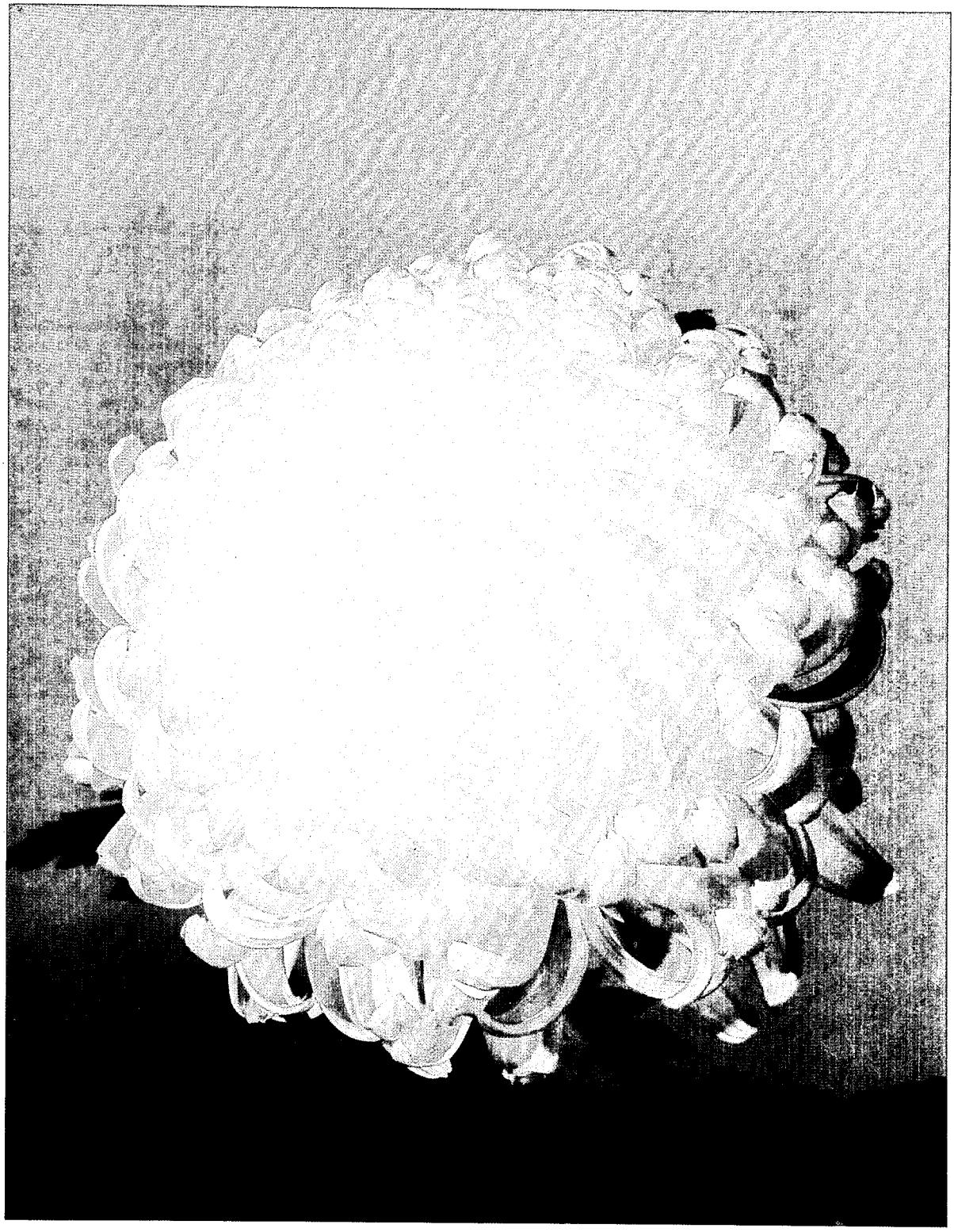

* * * * *